United States Patent
Redwood et al.

(10) Patent No.: US 6,611,962 B2
(45) Date of Patent: *Sep. 2, 2003

(54) ARTICLES WITH REMOVABLE ELEMENTS

(75) Inventors: Michael Redwood, Somerset (GB);
John D. Widdemer, Gloversville, NY (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/891,207

(22) Filed: Jun. 26, 2001

(65) Prior Publication Data

US 2001/0032347 A1 Oct. 25, 2001

Related U.S. Application Data

(63) Continuation of application No. 09/494,121, filed on Jan. 28, 2000, now Pat. No. 6,275,996.

(51) Int. Cl.⁷ ............................................ A41D 19/00
(52) U.S. Cl. ............................ 2/160; 2/161.4; 2/162; 600/15
(58) Field of Search .................... 2/162, 16, 161.1, 2/161.2, 161.4, 167; 128/878; 602/9, 14, 21, 22, 162, 64; 600/15; 82/44, 50; 607/111

(56) References Cited

U.S. PATENT DOCUMENTS

| | | |
|---|---|---|
| 499,891 A | 6/1893 | Schlesicky |
| 1,268,516 A | 6/1918 | Von Baldass |
| 1,374,257 A | 4/1921 | Van Raalte |
| 1,416,653 A | 5/1922 | Lenneberg |
| 1,416,654 A | 5/1922 | Lenneberg |
| 1,524,137 A | 1/1925 | Kastl et al. |
| 2,103,711 A | 12/1937 | Cole |
| 2,187,987 A | 1/1940 | Sherrick |
| 2,333,428 A | 11/1943 | Kinsey |
| 2,674,684 A | 4/1954 | Duncan |
| 2,685,021 A | 7/1954 | Duncan |
| 2,831,196 A | 4/1958 | Scheiber |
| 3,124,806 A | 3/1964 | Campbell et al. |
| 3,292,628 A | 12/1966 | Maxwell et al. |
| 3,632,966 A | 1/1972 | Arron |
| 3,636,568 A | 1/1972 | Stuner |
| 3,915,151 A | 10/1975 | Kraus |
| 4,042,975 A * | 8/1977 | Elliott, Jr. et al. ............... 2/19 |
| 4,162,672 A | 7/1979 | Yazaki |
| 4,240,157 A | 12/1980 | Peters |
| 4,281,389 A | 7/1981 | Smith |
| 4,387,838 A | 6/1983 | Jackson |
| 4,471,495 A | 9/1984 | Kruse et al. |
| 4,488,726 A | 12/1984 | Murray |

(List continued on next page.)

FOREIGN PATENT DOCUMENTS

| | | |
|---|---|---|
| GB | 2257634 A | 1/1993 |
| JP | 5-103842 | 4/1993 |
| JP | 6-134072 | 5/1994 |
| WO | WO 90/07734 | 7/1990 |
| WO | WO00/01263 | 1/2000 |

*Primary Examiner*—John J. Calvert
*Assistant Examiner*—Katherine Moran
(74) *Attorney, Agent, or Firm*—Swidler Berlin Shereff Friedman, LLP

(57) ABSTRACT

Broadly, the present invention is an article, such as a glove or watch, to be worn by a user. The article includes at least one removable element with a health enhancing component, a comfort enhancing component, or an electronic component. Upon mating the element to the article, the element is removably connected to the inside of the article. When the user disposes their a hand within the article, the element is in contact with the user's skin. The element can be disposed about the user's wrist or adjacent the back of the user's hand. In another embodiment, the invention includes a replacement watch band with the health enhancing, comfort enhancing, or electronic components. The health, comfort or electronic features of the components can be appreciated by the user, when the article or watch band is worn.

20 Claims, 12 Drawing Sheets

U.S. PATENT DOCUMENTS

| | | | |
|---|---|---|---|
| 4,501,265 A | | 2/1985 | Pescatore |
| 4,561,123 A | | 12/1985 | Hull |
| 4,587,956 A | | 5/1986 | Griffin et al. |
| 4,632,389 A | * | 12/1986 | Moss ........................ 272/119 |
| 4,652,141 A | | 3/1987 | Arai |
| 4,761,835 A | | 8/1988 | Chen |
| 4,766,611 A | | 8/1988 | Kim |
| 4,862,521 A | | 9/1989 | Mann |
| 4,911,433 A | * | 3/1990 | Walker et al. .............. 272/119 |
| 4,941,210 A | | 7/1990 | Konucik |
| 5,003,637 A | | 4/1991 | Lonon |
| 5,030,196 A | | 7/1991 | Inoue |
| 5,085,626 A | | 2/1992 | Frey |
| 5,117,508 A | | 6/1992 | Tod |
| 5,155,869 A | | 10/1992 | Ralli et al. |
| 5,187,814 A | | 2/1993 | Gold |
| 5,345,368 A | * | 9/1994 | Huff ............................... 2/19 |
| 5,353,439 A | | 10/1994 | Kurtz et al. |
| 5,448,777 A | * | 9/1995 | Lew ............................... 2/19 |
| 5,478,278 A | | 12/1995 | Greenblatt |
| 5,486,112 A | | 1/1996 | Troudet et al. |
| 5,486,680 A | | 1/1996 | Lieberman |
| 5,509,809 A | * | 4/1996 | Clay ........................ 272/119 |
| 5,530,967 A | | 7/1996 | Cielo |
| 5,617,583 A | | 4/1997 | Yates et al. |
| 5,623,731 A | | 4/1997 | Ehrgott et al. |
| 5,640,712 A | | 6/1997 | Hansen et al. |
| 5,642,739 A | | 7/1997 | Fareed |
| 5,655,223 A | | 8/1997 | Cozza |
| 5,667,422 A | | 9/1997 | Erwin |
| 5,684,284 A | | 11/1997 | Lee et al. |
| 5,688,183 A | | 11/1997 | Sabatino et al. |
| 5,715,539 A | | 2/1998 | Benecki et al. |
| 5,720,046 A | | 2/1998 | Lopez et al. |
| 5,730,658 A | * | 3/1998 | Kurtz et al. ................ 473/205 |
| 5,733,201 A | | 3/1998 | Caldwell et al. |
| 5,743,844 A | | 4/1998 | Tepper et al. |
| 5,762,241 A | | 6/1998 | Cross |
| 5,768,710 A | * | 6/1998 | Williams .................... 272/119 |
| 5,771,492 A | | 6/1998 | Cozza |
| 5,774,894 A | | 7/1998 | Yates et al. |
| 5,782,743 A | | 7/1998 | Russell |
| 5,802,615 A | | 9/1998 | Wenk |
| 5,812,500 A | | 9/1998 | Webb, Jr. |
| 5,813,971 A | | 9/1998 | Broderick |
| 5,838,642 A | | 11/1998 | Tully |
| 5,842,232 A | | 12/1998 | Parrish |
| 5,855,022 A | | 1/1999 | Storto |
| 5,871,406 A | | 2/1999 | Worrell |
| 5,882,292 A | | 3/1999 | Miyaguchi |
| 5,890,228 A | | 4/1999 | Wagner |
| 5,898,938 A | | 5/1999 | Baylor et al. |
| 5,898,943 A | | 5/1999 | Kim |
| 5,901,379 A | | 5/1999 | Hirata |
| 5,950,239 A | | 9/1999 | Lopez |
| 5,951,459 A | | 9/1999 | Blackwell |
| 6,014,775 A | | 1/2000 | Missry |
| 6,029,277 A | | 2/2000 | Picchione, II |
| 6,085,355 A | | 7/2000 | Chen |
| 6,119,271 A | * | 9/2000 | Byon ........................ 473/205 |
| 6,275,996 B1 | * | 8/2001 | Redwood et al. .............. 2/160 |
| 6,306,076 B1 | * | 10/2001 | Gill ............................. 600/15 |
| 6,344,021 B1 | * | 2/2002 | Juster et al. .................. 600/15 |

* cited by examiner

ARTICLES WITH REMOVABLE ELEMENTS

CROSS-REFERENCE TO RELATED APPLICATIONS

This application is a continuation application of the U.S. application Ser. No. 09/494,121, filed Jan. 28, 2000, now U.S. Pat. No. 6,275,996.

BACKGROUND OF THE INVENTION

1. Technical Field

The present invention generally relates to articles worn by a user, and more particularly, to gloves and watches with removable elements, such as bands or patches for use therewith.

2. Background Art

Many people develop painful ailments due to their age, a sports-injury, or execution of repetitive motions. These ailments inhibit their ability to participate in sports and perform various other motions during normal daily activities. These ailments include such problems as "golfer's or tennis elbow," carpal tunnel syndrome, arthritis in various joints and muscles and tendon problems. To reduce the effects of such ailments, many athletes wear devices, such as copper bracelets, magnetic bracelets, or cloth wraps that contain magnetic or far infra-red radiation amplifying minerals. These devices are often ill fitting and cumbersome so that athletes and other users find them distracting or inhibiting when worn during the performance of certain motions.

One solution to this problem is disclosed in U.S. Pat. No. 5,720,046 to Lopez et al. which discloses a therapeutic glove with magnets embedded therein and disposed at various locations within the glove such as the fingers, palm and back of the hand. These gloves would be difficult to wear while attempting to grip a tool or sports implement, since the magnets therein would interfere with the user's ability to grip and may prevent a snug fit such as that desired in many sports' gloves.

Therefore, a need exists for a compact, and secure way to provide the benefits associated with such materials without interfering with the user's performance.

Moreover, people who spend significant amounts of time outdoors can be exposed to a large range of temperatures. In such conditions, they prefer to maintain a reasonable range of hand temperatures to control precisely their dexterity and their grip on tools or sports implements. Many people now carry and use different types of gloves, light weight ones for warmer days and more bulky, lined gloves for colder days. This requires investing in two types of gloves and carrying two types of gloves on days when large temperature swings are expected. Therefore, a need also exists for gloves or other articles that can be used in a large range of temperatures to help maintain adequate hand temperature.

SUMMARY OF THE INVENTION

Broadly, the present invention is an article, such as a glove or watch, to be worn by a user. The article includes an article fastener disposed on the article's inner surface and at least one, separate removable element. The removable element has an inner surface including a complementary element fastener and an outer surface for contacting the user's skin. The element further includes a health enhancing component, a comfort enhancing component, or an electronic component. Upon mating the article fastener to the removable element fastener, the removable element is removably connected to the inside of the article. Upon the user disposing a hand within the article, the removable element is in contact with the user's skin.

In one embodiment, the element is a single layer or multi-layer structure, and the fasteners are of the hook-and-loop type. In another embodiment, the health enhancing component includes magnetic, copper, or far infra-red amplifying materials. In yet another embodiment, the comfort enhancing component includes terry cloth, leather, synthetic leather, fabric, foam, a gel pouch, fabric with temperature controlling materials, foam with temperature controlling materials, or a gel pouch with temperature controlling materials. In an additional embodiment, the electronic component performs a function selected from the group consisting of measuring heart rate, measuring blood pressure, measuring distance walked, measuring body temperature, measuring external temperature, measuring time, measuring strokes, measuring the speed of the user, or measuring the speed of the hand of the user.

The health enhancing, comfort enhancing and electronic components can be used singularly or in various combinations.

In one embodiment, the article is a glove and the element is a band that is configured to fit adjacent the wrist portion of the glove or the element is a patch configured to fit adjacent the back portion of the glove. The band and the patch can be used together or separately in one glove. The article can be provided with a set of bands or patches with different properties or combinations of health enhancing, comfort enhancing or electronic components.

The article, in another embodiment, is a watch and the element is a band that is secured to the inner surface of the watchband.

In another embodiment, the watch band itself includes the health or comfort enhancing components and is removably secured to a watch body.

BRIEF DESCRIPTION OF THE DRAWINGS

To facilitate the understanding of the characteristics of the invention, the following drawings have been provided wherein.

DESCRIPTION OF THE PREFERRED EMBODIMENTS

Figure 1:
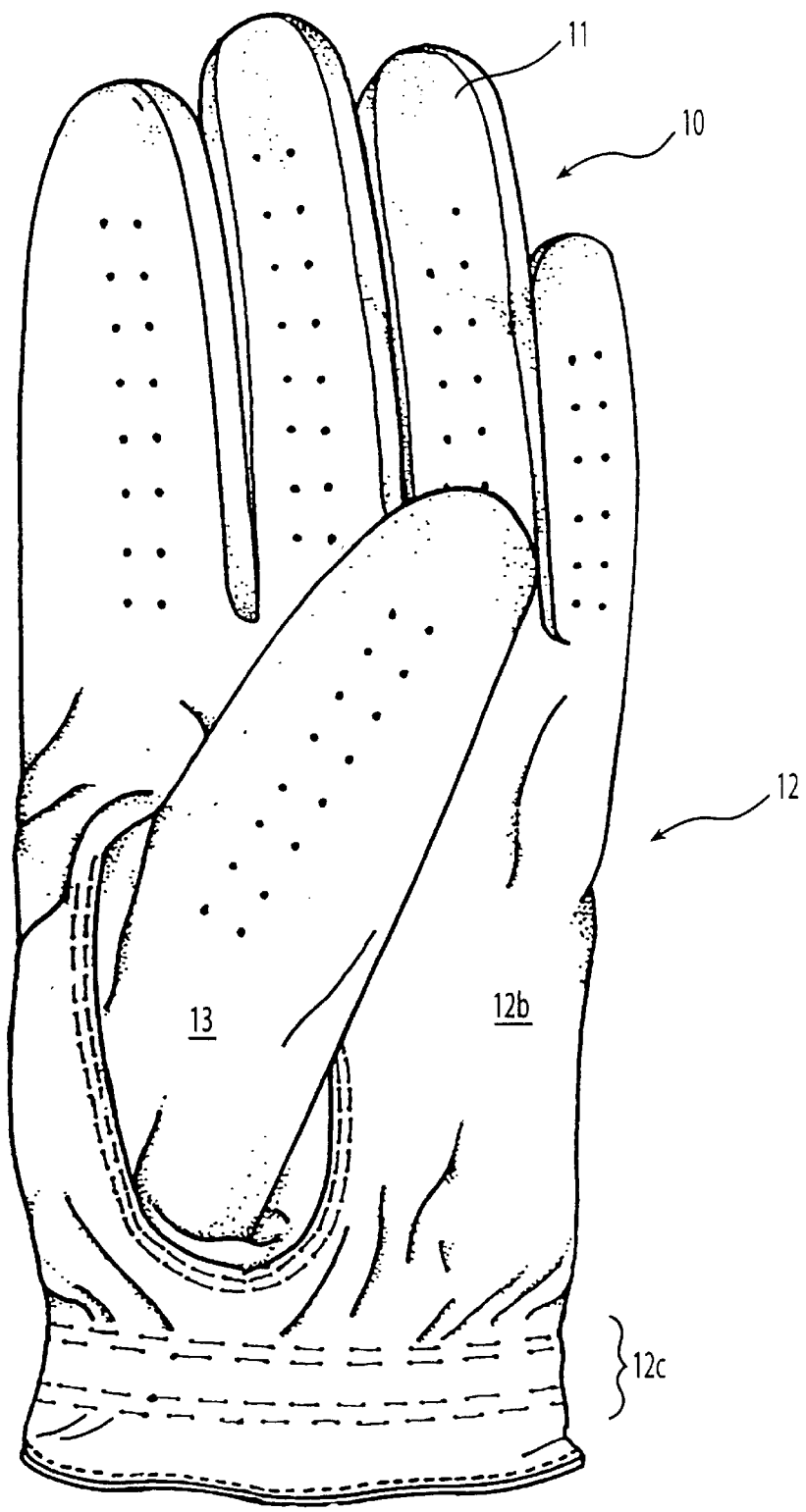
FIG. 1 is a front view of a glove of the present invention.
Figure 2:
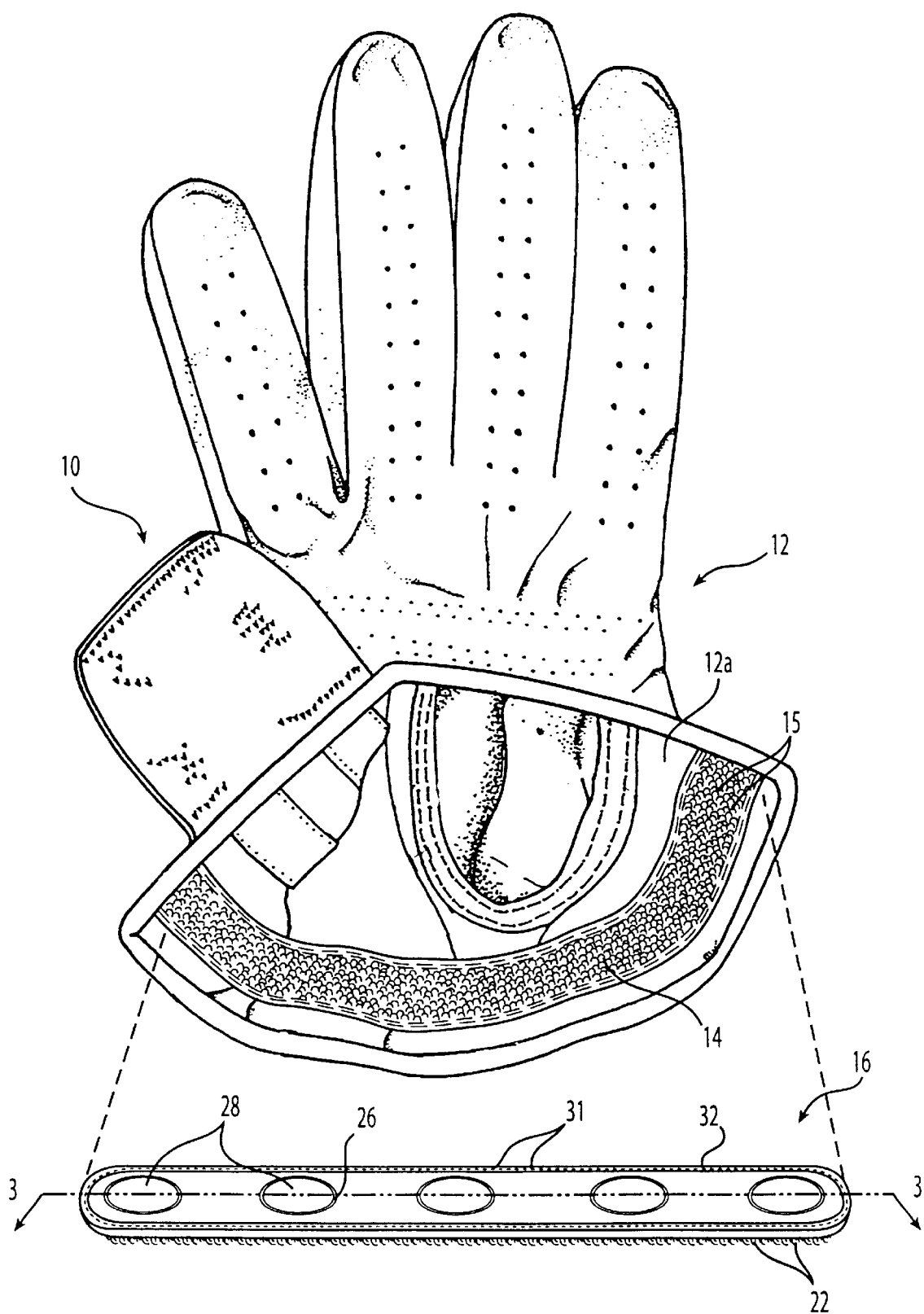
FIG. 2 is a back view of the glove of FIG. 1 with a flap open and a removable band with copper disks, wherein the band is in an uninstalled state.

Referring to the drawings, wherein like reference numbers are used to designate like parts, and as shown in FIGS. 1 and 2, a leather skin golf glove 16 is shown. The glove 10 includes finger casings 11, body portion 12 with inside surface 12a and outside surface 12b, and thumb casing 13. The body further includes a wrist portion 12c, which when a user inserts their hand within the glove, is adjacent the user's wrist. Thumb casing 13 is coupled to the body 12 by stitching in a conventional manner.

Referring to FIG. 2, the glove 10 further includes a fastener 14, which is a strip of material with loops 15 thereon. The fastener 14 is stitched to the inside surface 12a of the body 12 on the wrist portion 12c. The preferred fastener material is a soft, lightweight loop material, such as is commercially available from VELCRO USA, INC. of Manchester, N.H. under the designation style LP 3905. The fastener 14 material can be elastic or inelastic. Optionally, a separate elastic band can be sewn into the glove.

Figure 3:
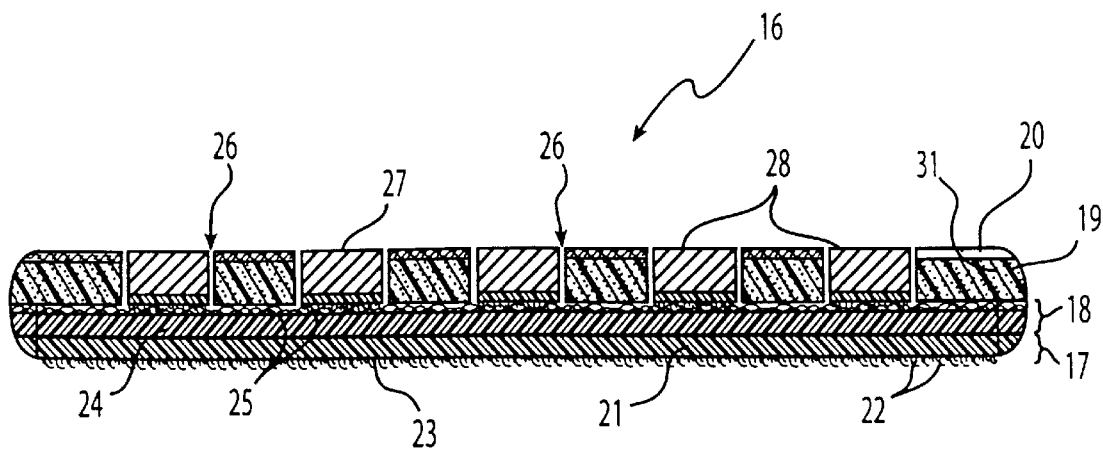
FIG. 3 is a cross-sectional view of the band shown in FIG. 2 along the line 3—3 of FIG. 2.

Referring again to FIG. 2, a removable band 16 with health and comfort enhancing components for use with the glove 10 is shown in an uninstalled state. Referring to FIGS. 2 and 3, the band 16 includes four layers 17–20. The first fastener layer 17 includes a strip of material 21 with fastener hooks 22 connected thereto. The hooks 22 are complementary to the loops 15 on the glove, and the preferred material for fastener layer 17 is a light weight hook material, such as is commercially available from VELCRO USA, Inc. of Manchester, N.H. under the designation style 805 and the hooks 22 are on the inner surface 23 of the band. Band 16 may be a longitudinally extending layer.

The second layer 18 is also a fastener layer and includes a strip of material 24 with plurality of loops 25 thereon. The strip 24 is adjacent to the strip 21 so that the loops 25 are opposite the hooks 22.

The third cushioning layer 19 of the band is formed to act as a comfort enhancing component and is formed of a foam. The foam optionally includes temperature controlling materials that are for example coated on or embedded within the foam. One preferred material contains a microencapsulated phase change material for maintaining a predetermined temperature. One most preferred material is Comfortemp® foam manufactured by Frisby Technologies, Inc. The cushioning layer 19 defines five holes 26 there through.

The fourth layer 20 is a fabric, such as a polyester fleece or an absorbent textile that forms a portion of the outer surface 27. Two examples of a preferred absorbent textile are CoolMax® supplied by Liberty Fabrics in New York or cotton terry cloth. The fourth layer 20 also enhances the user's comfort because it contacts the user's skin when the band is in use. The outermost layer's composition dictates how it provides comfort. For example, a terry cloth outer layer absorbs sweat.

Figure 4:
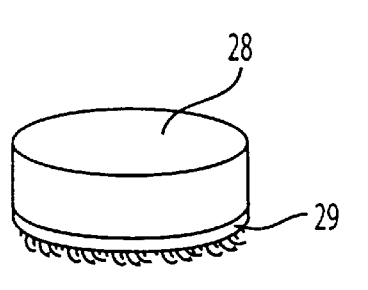
FIG. 4 is a perspective view of one copper disk from FIG. 2 including a fastener.
Figure 5:
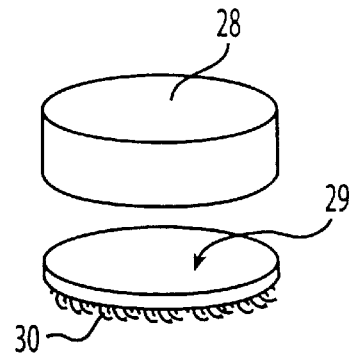
FIG. 5 is an exploded, perspective view of the copper disk and fastener of FIG. 4.

The band 16 further includes a health enhancing component which is in the form of copper disks 28. The copper disks 28 are received within the holes 26 of the cushioning layer 19. As shown in FIGS. 3–5, fastener material 29 is coupled to one side of each disk 28 by adhesive. One preferred fastener material 29 is manufactured by VELCRO USA, Inc. under the name Vel Coins. The material 29 includes hooks 30 complementary with the loops 25 on the second layer 18. When each disk 29 is disposed within the hole 26, the hooks 30 on the fastener material 29 releasably couple the disk to the fastener layer 18.

In another embodiment, the copper disks can be replaced with disks that include other health enhancing materials, such as magnetic material, far infra-red amplifying material, and the like. In yet another embodiment, disks with different health enhancing materials from one another can be used in a single band. For example, copper and magnetic disks can be used in a band together. Although five disks of copper material are shown, the present invention is not limited to this amount of health enhancing material.

As shown in FIGS. 2 and 3, stitches 31 couple the layers 17–20 together. These layers can also be coupled by other conventional means such as adhesive. The band 16 further includes piping 32 around the edges.

Figure 6:
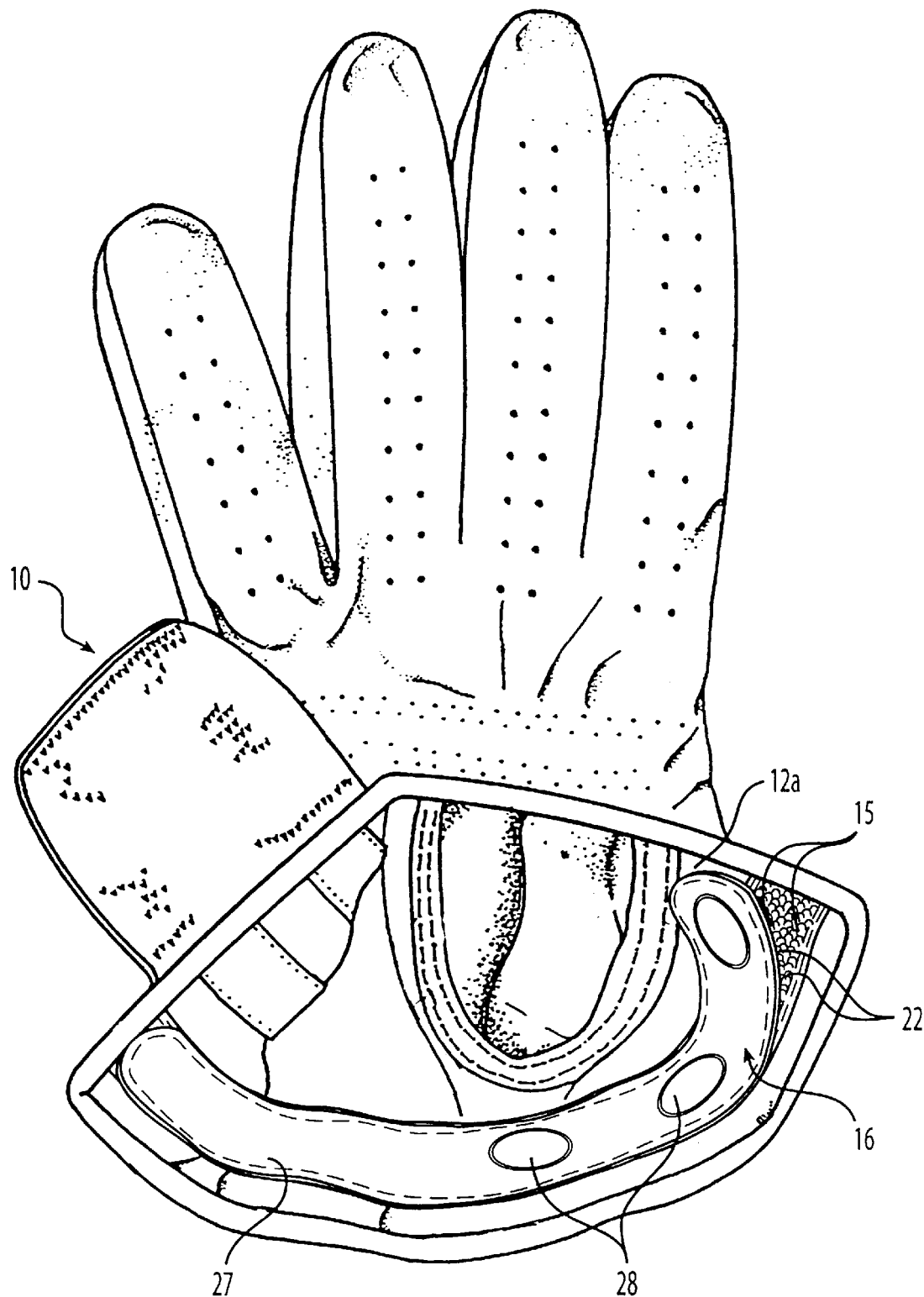
FIG. 6 is a back view of the glove of FIG. 2 with the flap open, wherein the removable band is in a partially installed state.

Referring to FIG. 6, when a user disposes the band 16 within the glove 10, the fastener hooks 22 on the band mate to the glove fastener loops 15. Thus, the band 16 is removably connected to the fastener loops 15 and consequently the glove 10. Upon the user disposing their hand within the glove 10, the band 16 is located about the user's wrist and the outer surface 27 of the band and the copper disks 28 are in contact with the user's skin. In another embodiment, the copper disks can be disposed below the fabric layer 20 (shown in FIG. 3).

In one embodiment, the length of the band can be less than the circumference of the user's wrist. In another embodiment, the length of the band can be substantially equal to the circumference of the user's wrist.

Figure 7:
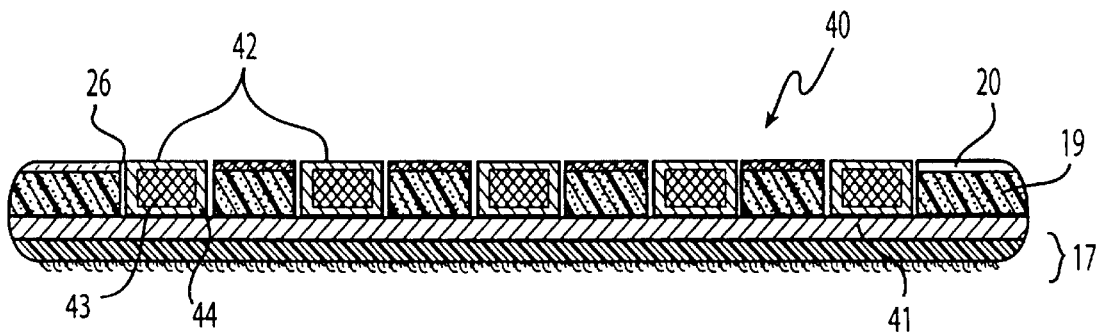
FIG. 7 is a cross-sectional view of an alternative embodiment of the band including magnetic disks.

With reference to FIG. 7, another embodiment of a band 40 with health and comfort enhancing components is illustrated for use with the glove 10 shown in FIG. 2. The band 40 has four layers 17, 19, 20, and 41, where the fastener layer 17, and the cushioning and fabric layers 19 and 20 are as described above. However, the layer 41 is a flexible, metallic strip formed of a material such as copper foil.

The band 40 further includes magnetic disks 42 that are received by the holes 26 in the cushioning layer 19. The magnetic disks are formed of a core disk 43 of neodymium that is surrounded by a chrome plating 44 for protecting the magnetic core 43. One preferred magnetic disk is manufactured by Arnold Engineering. However, other, permanent magnetic materials can be used. It is preferred that the magnetic material has a strength of greater than about 800 gauss per square inch and more preferably between about 1000 and about 2500 gauss per square inch. When the magnetic disks 42 are disposed in the holes 26, the magnetic disks 42 contact the metallic strip layer 41 and the magnetic attraction of the disk to the strip removably secures each magnetic disk within the band 40. The band 40 is used similarly to the band 16.

Figure 8:
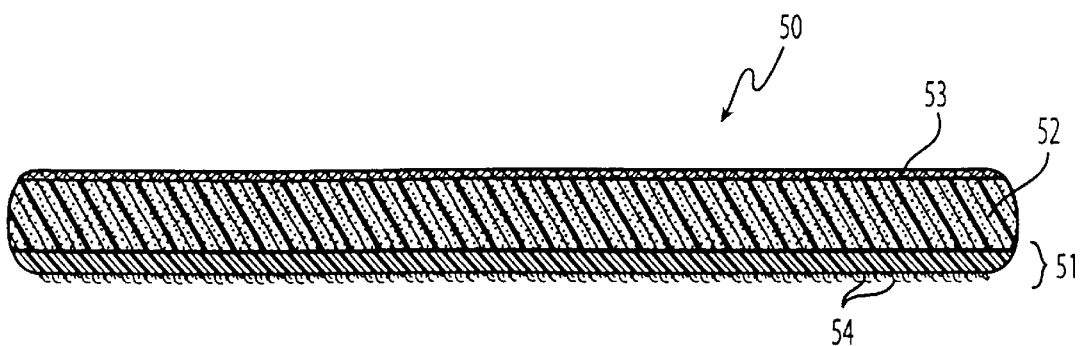
FIG. 8 is a cross-sectional view of an alternative embodiment of the band including foam with temperature controlling material.

With reference to FIG. 8, another embodiment of a band 50 with comfort enhancing components is illustrated for use with the glove 10 shown in FIG. 2. The band 50 has three layers 51–53. The first layer 51 includes the hooks 54, as discussed above. The second layer 52 is a foam, cushioning layer that optionally includes temperature controlling materials, as discussed above. The third layer 53 is a fabric layer, as discussed above. The band 50 is used similarly to the band 16.

Figure 9:
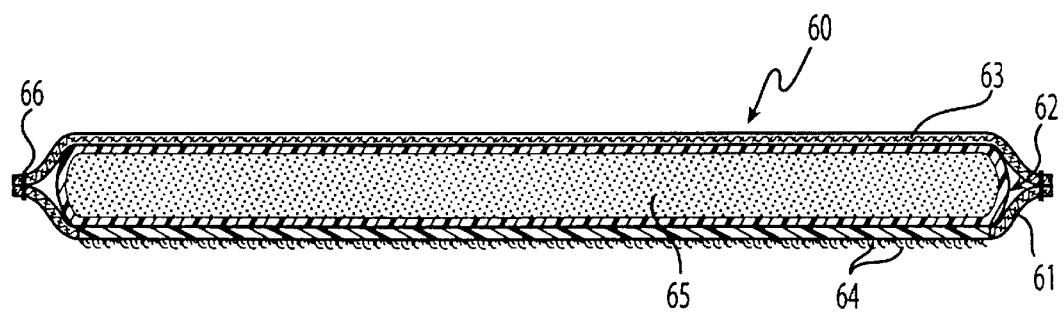
FIG. 9 is a cross-sectional view of an alternative embodiment of the band including a pouch with a temperature controlling gel therein.

With reference to FIG. 9, another embodiment of a band 60 with a comfort enhancing component is illustrated for use with the glove 10 shown in FIG. 2. The band 60 has three layers 61–63. The first, fastener layer 61 includes hooks 64, as discussed above. The second cushioning layer 62 is a pouch. The pouch 62 includes, for example, a plastic pouch filled with temperature controlling or temperature responsive materials 65.

One preferred material is a warming material that upon activation by oxygen stays hot for about seven (7) hours, such as HEAT manufactured by Mitubishi of Japan. Another material is Intelligel® manufactured by Dicon Technologies. These materials can also include a moisture management material. The third layer 63 is a fabric layer, as discussed above. The band 60 is constructed so that the stitches 66 connect the first and third layers 61 and 63 together about the edges so that the gel pouch 62 is retained there between. The band 60 is used similarly to the band 16.

Figure 10:
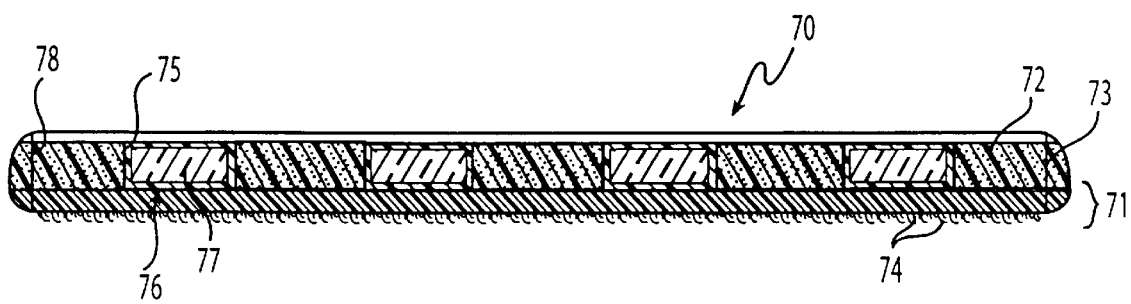
FIG. 10 is a cross-sectional view of an alternative embodiment of the band including foam with temperature controlling material and packets containing far infra-red amplifying material.

With reference to FIG. 10, another embodiment of a band 70 with a comfort enhancing component is illustrated for use with the glove 10 shown in FIG. 2. The band 70 has three layers 71–73. The first layer 71 includes the hooks 74, as discussed above. The second layer 72 is a foam layer that optionally includes temperature enhancing materials, as discussed above. The cushioning layer 72 defines four holes 75. The third layer 73 is a fabric layer, as discussed above.

The band 70 further includes plastic pouches 76 that contain far infra-red amplifying materials 77, also known as far infra-red emitting materials. The pouches 76 are received in the holes 75 in the cushioning layer 72. The far infra-red amplifying materials include various minerals, known in the art and commercially available. One preferred material is ZER manufactured by ZER of Korea. This material amplifies and reflects infra-red waves emitted from the human body back to the human body. This material is a mixture of rare earth elements such as erbium, titanium and neodymium. The band 70 is constructed so that the stitches 78 connect the layers 71–73 together about the edges, and the pouches 76 are retained within the band. The band 70 is used similarly to the band 16.

Figure 11:
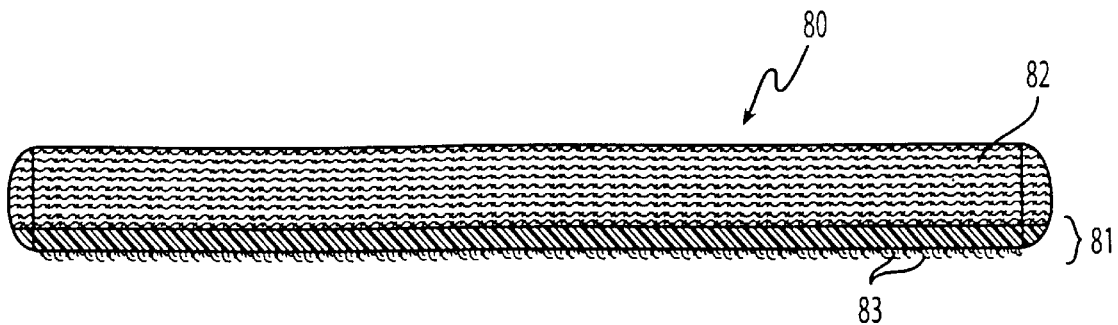
FIG. 11 is a cross-sectional view of an alternative embodiment of the band including a fabric layer.

With reference to FIG. 11, another embodiment of a band 80 with a comfort enhancing component is illustrated for use with the glove 10 shown in FIG. 2. The band 80 has two layers 81 and 82. The first, fastener layer 81 includes the hooks 83, as discussed above. The second layer 82 is a fabric layer as discussed above. In another embodiment, foam can be used for the second layer. The layers of the band 80 are stitched together, and the band 80 is used similarly to the band 16.

Figure 12:
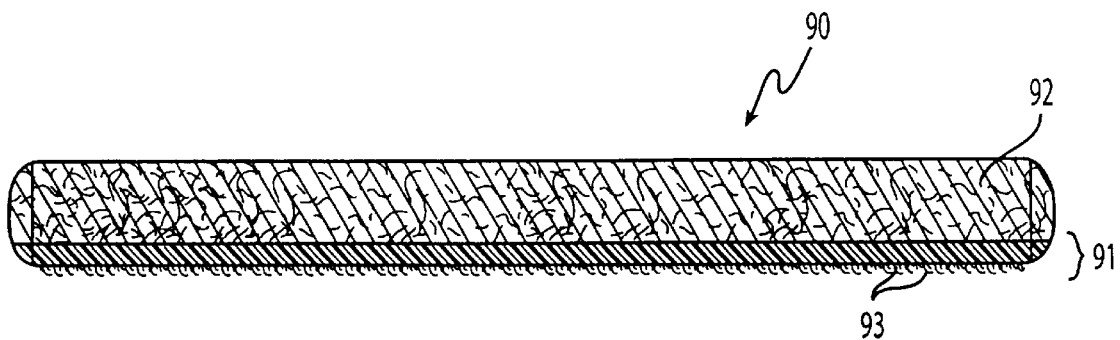
FIG. 12 is a cross-sectional view of an alternative embodiment of the band including a leather or synthetic leather layer.

With reference to FIG. 12, another embodiment of a band 90 with a comfort enhancing component is illustrated for use with the glove 10 shown in FIG. 2. The band 90 has two layers 91 and 92. The first, fastener layer 91 includes the hooks 93, as discussed above. The second layer 92 is a leather or synthetic leather layer. The layer 92 can optionally include a temperature controlling material such as embedded microencapsulated phase change material or a coating with microencapsulated phase change material therein. One preferred microencapsulated phase change material is manufactured by Frisby Technologies, Inc. of Freeport, N.Y. under the name THERMASORB® 83. Other THERMASORB® formulations can also be used for higher or lower activation temps. The layer 92 can also optionally include a health enhancing material such as magnetic or copper disks or embedded magnetic powder or far infra-red amplifying material. The layers of the band 90 are stitched together, and the band 90 is used similarly to the band 16.

Figure 13:
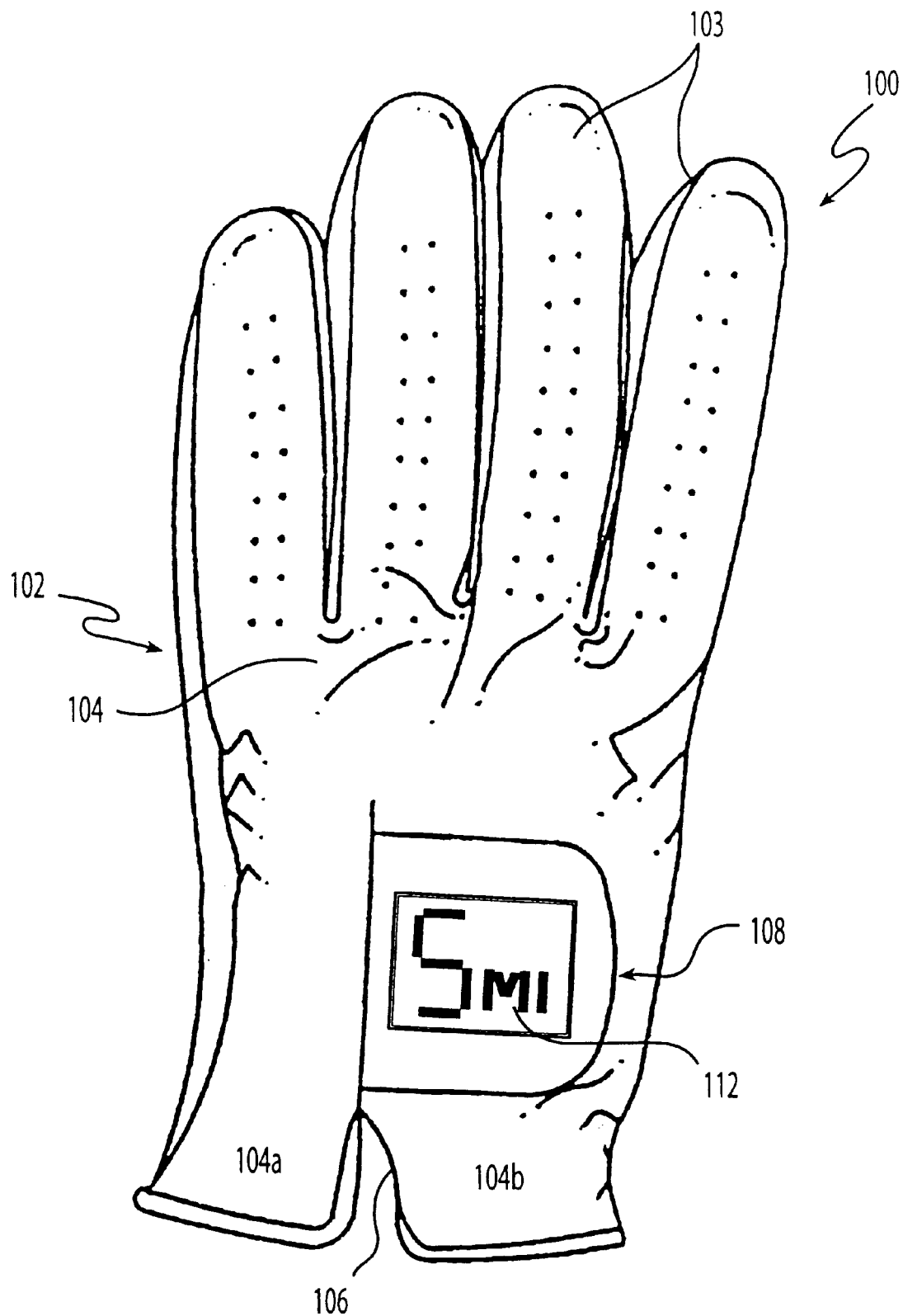
FIG. 13 is a front view of an alternative embodiment of the glove of the present invention that includes electronics.
Figure 14:
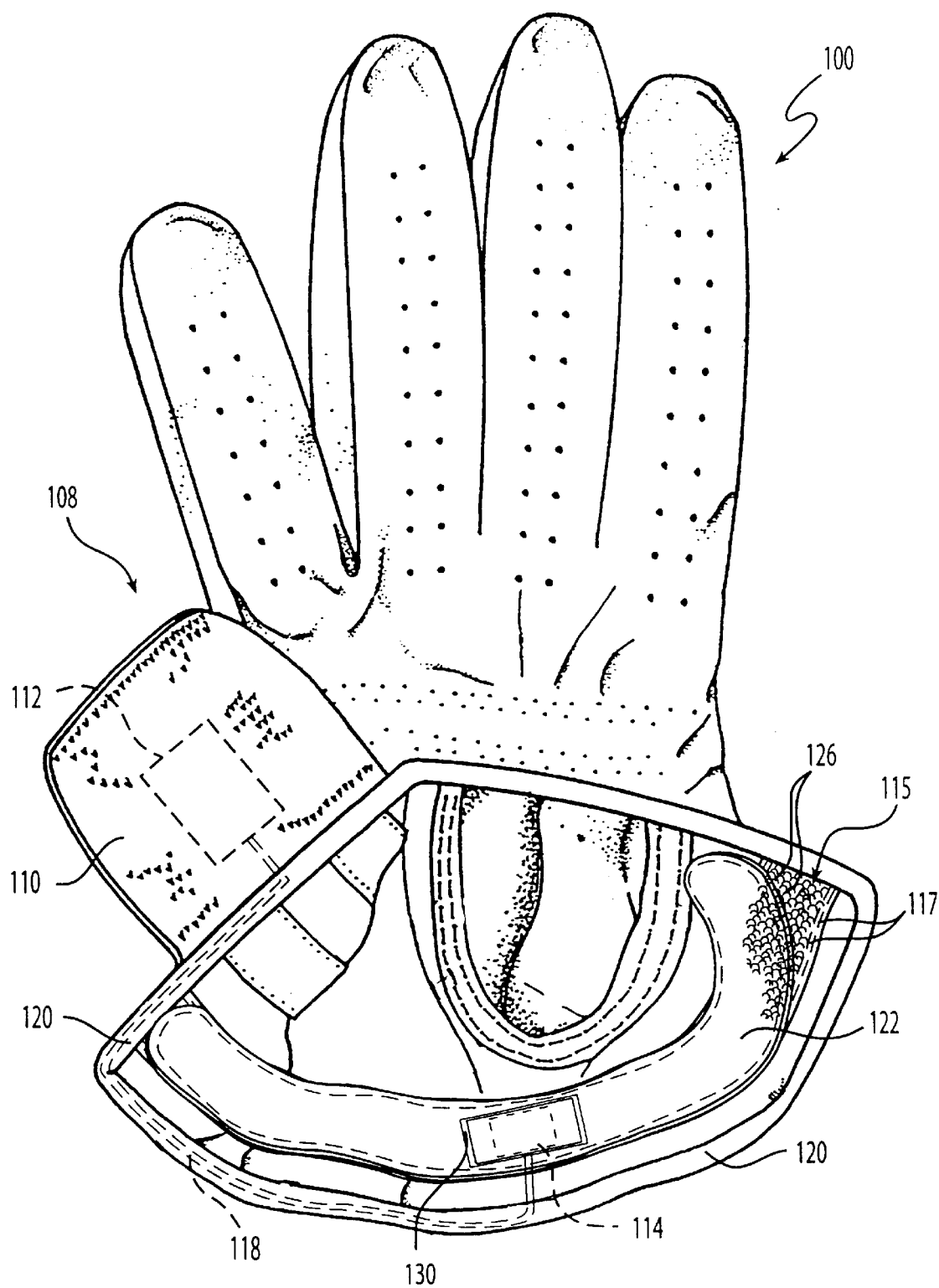
FIG. 14 is a back view of the glove of FIG. 13 with the flap open, wherein the removable band is in a partially installed state.

Turning to FIG. 13, another embodiment of a glove 100 is shown. The glove 100 includes a body 102, and finger casings 103. Back body portion 104 comprises two sections 104a, 104b separated by back opening 106. Back opening 106 eases pulling glove 100 on the user's hand. Once the hand is inside glove 100, adjustable closure 108 is closed. Closure 108 includes hook or loop pad 110 (as shown in FIG. 14). The body portion 104b has a complementary hook or loop pad (not shown) for securing the closure 108 to body portion 104b. Closure 108 may have hook material on the inside surface and loop material can be on the body portion 104b or vice versa.

The closure 108 further includes a display screen 112 secured therein, which can for example be a liquid crystal display for showing alphanumeric data. Various display components are commercially available and known by those of ordinary skill in the art. In another embodiment, the display screen can be located in another part of the glove. Controls can also be mounted on the glove either separately from the screen or integral therewith.

Referring to FIG. 14, the glove 100 further includes a metallic contact 114 (shown in phantom) connected to outer surface of the fastener strip 115. The fastener strip 115 is connected to the glove inner surface, as discussed above, and includes loops 117. A suitable electric wire 118 (shown in phantom) electrically connects the display component 112 to the metallic contact 114 so that these components are in electrical communication. The wire 118 extends between the layers of the closure 108 and within the piping 120 on the edges of the glove.

Figure 15:
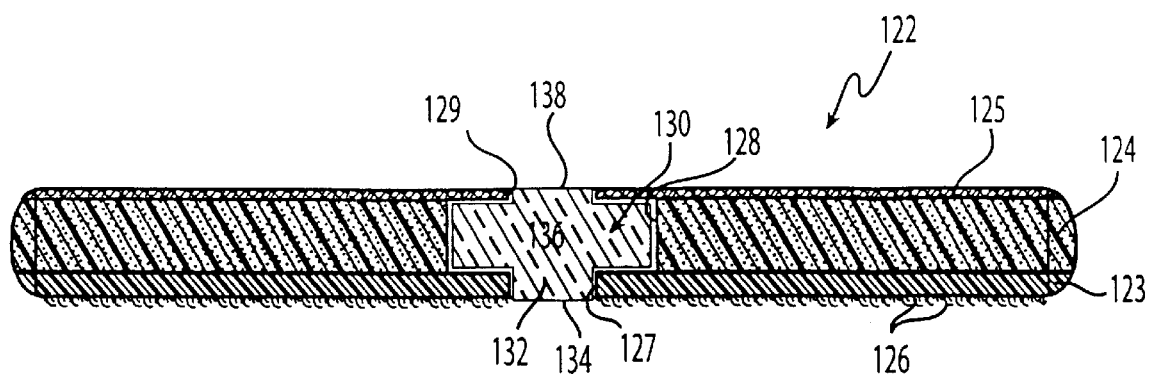
FIG. 15 is a cross-sectional view of the band including electronics shown in FIG. 14.

Referring to FIGS. 14 and 15, the glove further includes a removable band 122. The band has three layers 123–125. The first, fastener layer 123 includes the hooks 126, as discussed above. The fastener layer 123 further defines a window 127 there through. The second, cushioning layer 124 is a foam layer that optionally includes temperature controlling or responsive materials, as discussed above. The cushioning layer 124 defines a window 128 there through. In another embodiment, the cushioning layer can be formed of another material such as fabric, leather or with a gel pouch therein. The third layer 125 is a fabric layer, as discussed above. The fabric layer 125 defines a window 129.

The band 10 further includes an electronic component 130. The electronic component 130 includes a metallic contact 132 that is stepped and forms the inner exposed surface 134 of the component. The contact 132, band 122 and glove 100 are configured and dimensioned so that when the band is disposed within the glove the contacts 132 and 114 are in good electrical contact. The contact 132 is in electrical communication with the internal circuitry and elements of the component 130. When the component 130 is disposed within the windows 127, 128 and 129, the component is securely retained within the band 122 and the surfaces 134 and 138 are contactable. The surface 138 will be in contact with the user's skin, when the band 122 is in use. In another embodiment, the band 122 can be changed so that the component 130 is not in contact with the user's skin in use, for example, by disposing the component beneath a fabric layer.

The internal circuitry and elements of the component 130 are within the central portion 136 and include any sensors, microprocessors, timers, or transducers, etc., as necessary to preform the desired function of the component 130. The function of the electronic component 130 can be at least one of the following: measuring heart rate, measuring blood pressure, measuring distance walked, measuring body temperature, measuring external temperature, measuring time, measuring strokes, measuring speed of user, storing information, or measuring speed of the hand of the user, etc. Electronic components that perform a combination of these functions can also be used. Various electronic components for performing these functions are commercially available and known by those of ordinary skill in the art.

Referring to FIG. 14, when the band 122 is installed in the glove 100, the loops 117 and hooks 126 mate to removably secure the band 122 to the glove 100. The electrical component 130 is in electronic communication with the display 112 via the wire 118 and the metal contacts 114 and 132 (shown in FIG. 15). The user can then wear the glove 100, and the band 122 surrounds their wrist. If the electronics provide distance information, for example, then the user can walk on the golf course and know how far they walked as indicated on the display 112. In another embodiment, known infra-red technology can be used to communicate information between the electronic component 130 and the display 112. Infrared technology can also be used to provide a data port on the display 112 and/or electronic component 130 so that data can be passed from these components to an external, microprocessor, personal computer, display, printer, or the like.

In another embodiment, the glove 100 instead of including the display can have an electronic component with an audio chip for telling the user the information when the user actuates the electronics by for example depressing a button or issuing a vocal command. The display can also be replaced with an infra-red or hard wired data port. In another embodiment, the glove 100 can be used with the other bands discussed above.

Sets of bands with health, comfort and electronic components can be provided for use with the glove 10.

Figure 16:
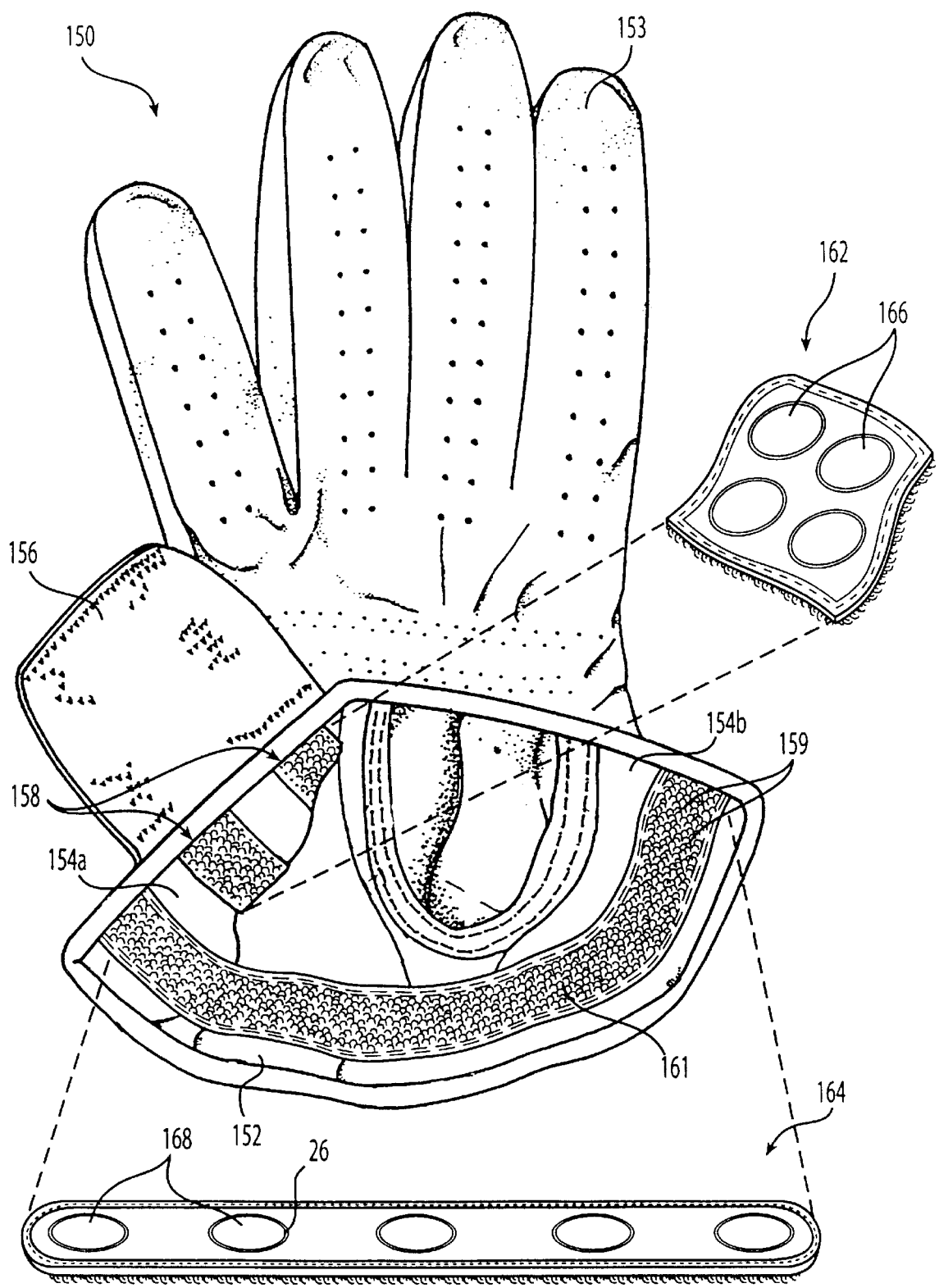
FIG. 16 is a back view of an alternative embodiment of the glove with the flap open, wherein a removable patch and a removable band are in an uninstalled state.

Turning to FIG. 16, another embodiment of a glove 150 is shown. The glove 150 includes a body 152, and finger casings 153. Back body portion 154 comprises two sections 154a, 154b separated by back opening. Once the hand is inside glove 150, adjustable closure 156 is closed. Closure 156 and body portion 154b are similar to that discussed above.

The back body portion 154a further includes fasteners 158 and 159, which are strips of material with loops 160 and 161, respectively, thereon. Fastener materials 158 are stitched to the inner surface of body 154a on a portion that will be adjacent to the back of a user's hand when the glove is closed. The fastener materials 158 are beneath the closure 156, when the glove is closed. Fastener material 159 is stitched to body 154a and 154b on the wrist portion of the glove. The preferred fastener materials were previously discussed. Any number of pieces of fastener material 158 can be used in the back of the hand section instead of two, such as one or three.

A removable patch 162 and a removable band 164 are for use with the glove 150, but are shown uninstalled. The patch 162 and the band 164 include four layers and removable magnets 166 and 168, as discussed above, with reference to FIGS. 2 and 3. The patch 162 and the band 164 further include fasteners 170 and 172 complementary to the fasteners 158 and 159, respectively. When the patch 162 is installed in the glove, it will be connected to the fasteners 158 and disposed so that the magnets 166 therein are in contact with the back of a user's hand. When the band 164 is installed in the glove, it will be connected to the fasteners 159 and disposed so that the magnets 168 therein are in contact with the wrist portion of a user's hand.

Sets of patches and bands with different health, comfort and electronic components can be provided for use with the glove 150. In this embodiment, the patches and bands can further include combinations of health and comfort materials or electronics, as discussed with reference to FIGS. 7–12, and 15. In addition, the glove can be configured to receive only the patch or a set of patches.

Figures 17, 18, 19:
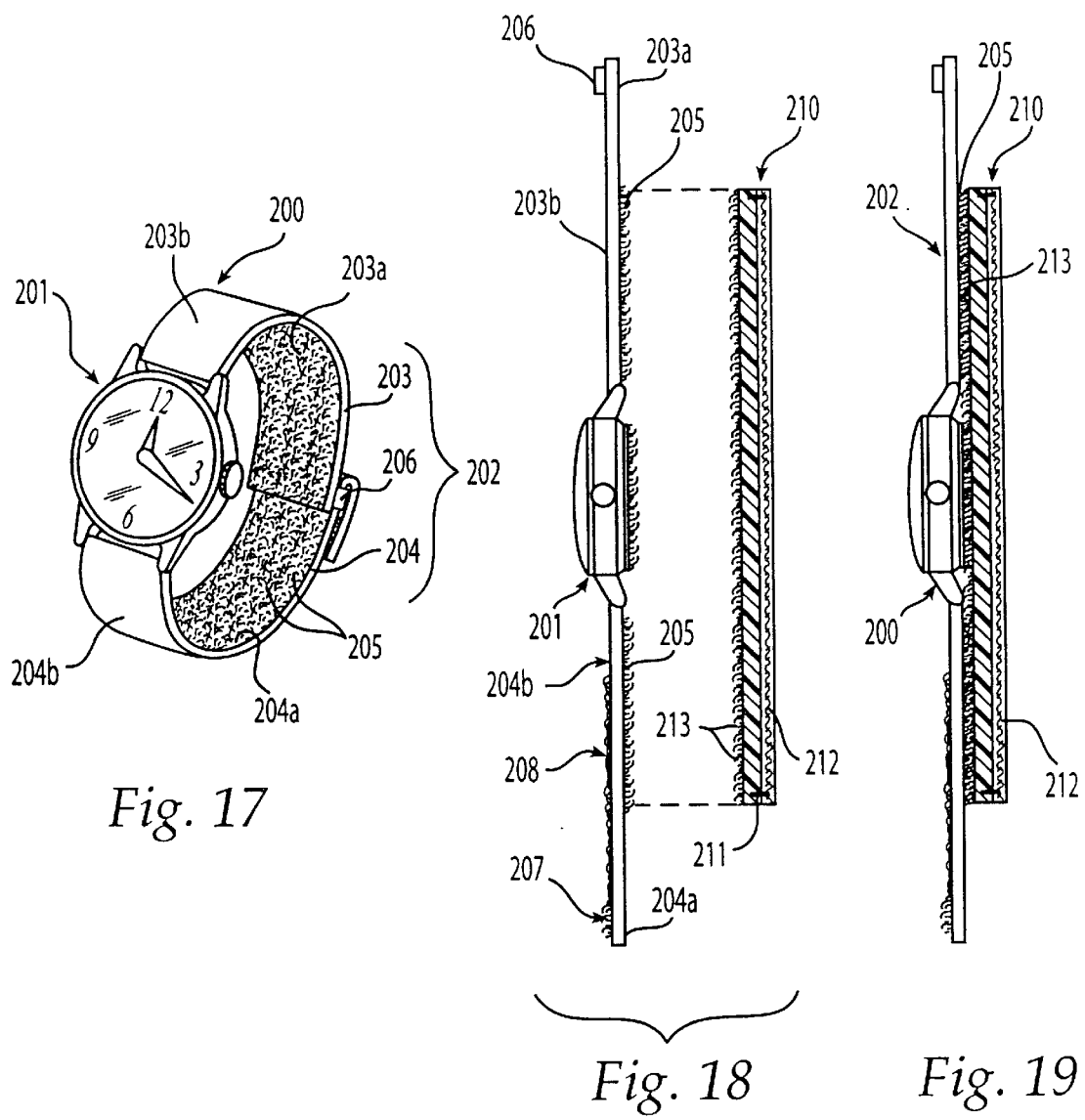
FIG. 17 is a perspective view of a watch of the present invention with the removable band removed for clarity.
FIG. 18 is an exploded, side view of the watch of FIG. 17 with the removable band uninstalled.
FIG. 19 is a side view of the watch of FIG. 17 with the removable band installed.

Referring to FIG. 17, a watch 200 is shown which includes a conventional watch body 201 and a resilient watch band 202 connected to the body 201 in a conventional fashion. The watch band 202 has two straps 203 and 204 with inner surfaces 203a, 204a and outer surfaces 203b, 204b. The inner surfaces 203a, 204a of the watch band include a fastener material that includes a strip with hooks 205 thereon. The strip with hooks 205 is secured to the inner surface of the watch band 202 by conventional means such as adhesive, sewing, or ultrasonic welding and the like, depending on the material of the watch band and strip. If the band is formed of plastic, the hooks can be integrally molded with the band.

Referring to FIGS. 17–19, the outer surface 203b of the strap 203 near the free end has a loop 206 disposed thereon. The outer surface 204b of the strap 204 has a fastener material 207 with hooks disposed thereon and a fastener material 208 with loops disposed thereon. The loop 206, and materials 207 and 208 are fastened in a conventional manner to the straps, as discussed above with respect to the hooks 205.

When the user wants to secure the watch 200 to their wrist they dispose the free end of the strap 204 through the loop 206 and fold the strap so that the hooks 207 mate with the loops 208 and secure the straps 203 and 204 together.

The watch 200 further includes a removable band 210 with health, comfort electronic components similar to the bands discussed above. The removable band 210 has two layers 211 and 212. The first, fastener layer 211 includes the loops 213. The second layer 212 is a fabric or cushioning layer as discussed above. The layers of the band 210 are stitched together. The band 210 is removably secured to the watch band 202, when the loops 213 on the band mate with the hooks 205 on the watch band. When the user secures the watch 200 to their wrist with the band 210 therein, the layer 212 contacts their skin and provides comfort to the user. The other bands described above with respect to gloves 10 and 100 can also be used with the watch 200.

Sets of removable bands with different properties can be provided for use with the watch.

In another embodiment, the watch can be any other conventional style watch with a buckle or clasp and with a watch band formed of various materials such as metal, leather or synthetic leather, cloth, plastic and the like. The watch body can include functions such as digital or analog time display, timing, calculating, heart rate monitoring, pacing, distance measurement, and the like alone or in combination.

Figure 20:
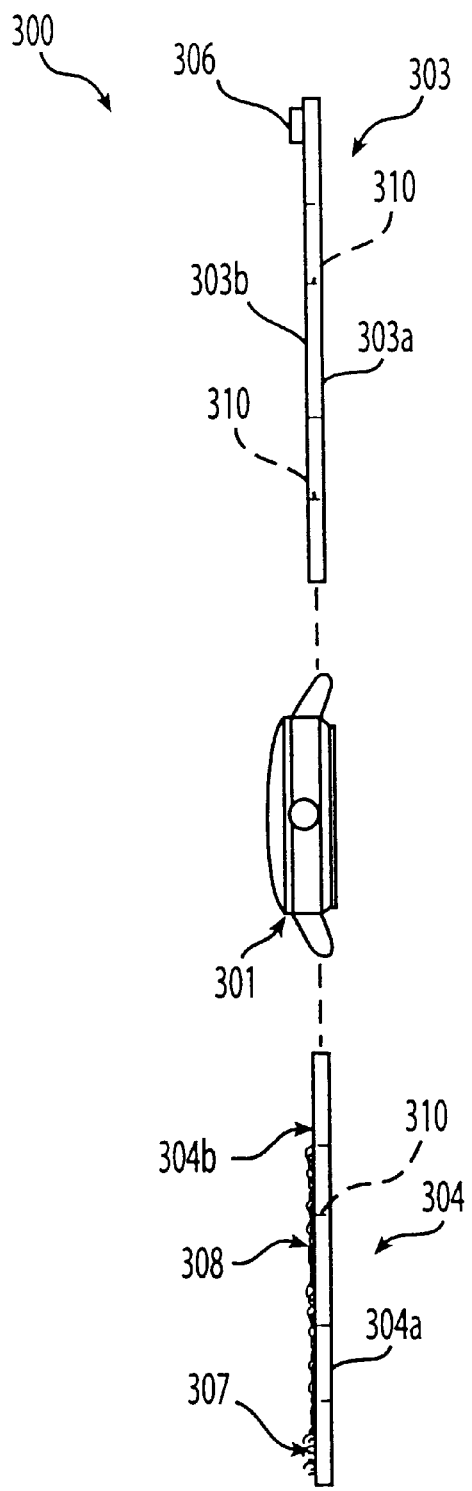
FIG. 20 is an exploded, side view of a watch with an alternative embodiment of the present invention, wherein a removable, watch band contains a health enhancing component.
Figure 21:
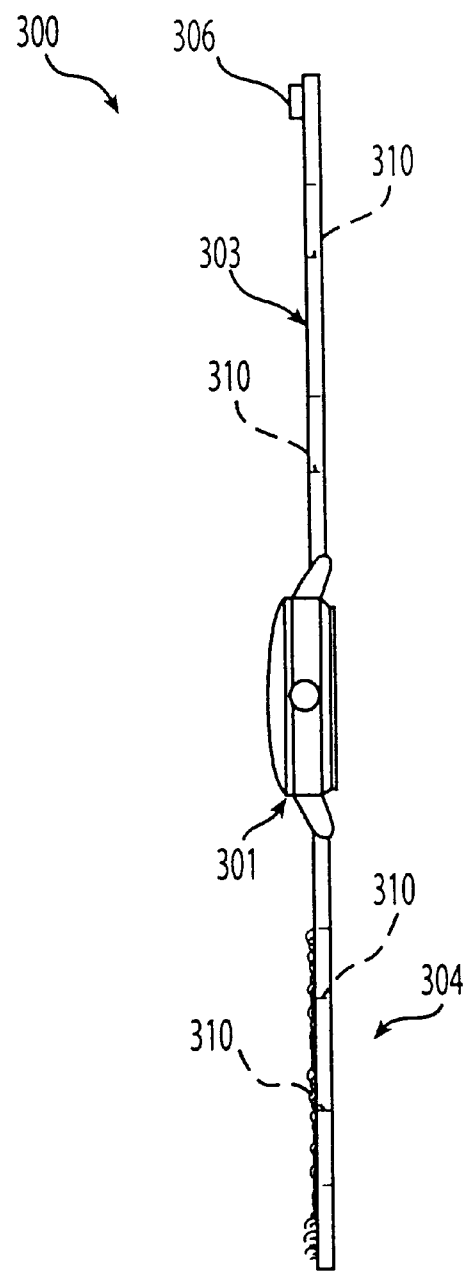
FIG. 21 is a side view of the watch of FIG. 20 with the removable, watch band connected to a watch body.

Referring to FIGS. 20–21, another embodiment of a watch 300 according to the present invention is shown. The watch 300 includes a conventional watch body 301 and two resilient watch band straps 302 that are connectable to the body 201 in a conventional fashion. The watch band 302 has two straps 303 and 304 with inner surfaces 303a, 304a and outer surfaces 303b, 304b. The outer surface 303b of the strap 303 near the free end has a loop 306 disposed thereon. The outer surface 304b of the strap 304 has a fastener material 307 with hooks disposed thereon and a fastener material 308 with loops disposed thereon. The loop 306, and materials 307 and 308 are fastened in a conventional manner to the straps, as discussed above with respect to the watch 200.

When the user wants to secure the watch 200 to their wrist they dispose the free end of the strap 304 through the loop 306 and fold the strap so that the hooks 307 mate with the loops 308 and secure the straps 303 and 304 together. Other conventional clasps can also be used.

The straps further include magnetic disks 310 (shown in phantom) disposed therein. Other health enhancing or comfort enhancing materials can be disposed within the straps, as discussed above. In this embodiment the materials are shown within the surfaces 303b and 303a and 304ba and 304a so that the materials would not contact the user's skin. In other embodiments the straps can be configured so that the magnetic disks can contact the user's skin and/or the magnetic disks can be removable from the band so that the health enhancing materials can be varied on one strap. Where the health materials are removable from the straps they can be joined thereto by hook and loop fasteners, magnetic attraction and the like. Where the health materials are fixed to the straps they can be joined thereto by molding them within the straps, adhesive, ultrasonic welding, and the like. The comfort enhancing materials can form one of the layers of the straps and include the health enhancing materials therein, as discussed with respect to the removable bands for use with the glove embodiments.

Thus, replacement bands can be provided for existing watches. The replacement watch bands can have more than one layer as discussed above or the bands can modify conventional cloth, leather, metal, etc. bands with the health, comfort, or electronic components.

While it is apparent that the invention herein disclosed is well calculated to fulfill the objects above stated, it will be appreciated that modifications and embodiments may be devised by those skilled in the art. For example, a three-piece glove including a two-piece body and separate thumb casing is shown however, various other glove constructions are within the scope of this invention such as those with an integral body and thumb casing. In addition, the present invention includes articles, such as gloves, watches, mittens, shoes, shirts, coats and other garments, and the like. Gloves can include sports gloves such as, hockey gloves or batting gloves, etcetera, or work gloves, dress gloves and the like. Although the hooks and loops are shown on various surfaces in the embodiments above, their locations can be reversed. The health enhancing materials can also be in various forms such as resin-embedded powder, sheets and the like. The number of fasteners and removable elements can be varied from these disclosed. The location of the removable elements can be anywhere with the glove where the components provide benefits. The removable bands or patches can also have a single layer structure, so that the fasteners are integrally formed with the bands and the components are secured thereto. The embodiments above can be modified so that some features of one embodiment are used with the features of another embodiment. It is intended that the appended claims cover all such modifications and embodiments as fall within the true spirit and scope of the present invention.

What is claimed is:

1. An article to be worn by a user, the article comprising:
   at least one article fastener disposed on the article; and
   a plurality of layers including at least one longitudinally extending layer having at least one component selected from the group consisting of: a health enhancing component, a comfort enhancing component, and an electronic component;
   wherein the article fastener removably attaches the plurality of layers to the article.

2. The article of claim 1, wherein the article fastener is a hook and loop type fastener.

3. The article of claim 1, wherein the article has an interior surface and the article fastener is positioned on the interior surface.

4. The article of claim 1, wherein the longitudinally extending layer is a flexible band.

5. The article of claim 1, wherein the component is a health enhancing component selected to alleviate the effects of ailments of the musculoskeletal system.

6. The article of claim 1, wherein the longitudinally extending layer is in contact with the user's skin when the article is worn.

7. The article of claim 1, wherein the article is a glove and the layer is a band disposable in a wrist portion of the glove.

8. The article of claim 1, further comprising an article body including a portion that at least partially covers an appendage when worn.

9. The article of claim 1, wherein said plurality of layers encompasses the at least one component.

10. The article of claim 1, wherein said plurality of layers further includes a cushioning layer.

11. A longitudinally extending layer element for use within an article to be worn by a user, the article having a first fastener, the layer comprising:
    a second fastener complementary with the first fastener, and at least one component selected from the group consisting of: a health enhancing component, a comfort enhancing component, and an electronic component, said at least one component being coupled to the second fastener,
    wherein the second fastener removably attaches the longitudinally extending layer to the article.

12. The layer of claim 11, wherein the longitudinally extending layer extends a length sufficient to at least partially cover a user's wrist when the article is worn by the user.

13. The layer of claim 11, wherein the component is removably attached to the layer.

14. The layer of claim 13, further comprising a component fastener and the component fastener attaches the at least one component to the layer.

15. The layer of claim 11, wherein the at least one component is health enhancing and selected from the group consisting of magnetic material, far infra-red amplifying material, and copper material.

16. The layer of claim 11, wherein the at least one component is electronic and includes a function selected from the group consisting of measuring heart rate, measuring blood pressure, measuring distance walked, measuring body temperature, measuring external temperature, measuring time, measuring strokes, measuring speed of user, and measuring speed of the hand of the user.

17. The layer of claim 11, further comprising a cushioning layer.

18. The layer of claim 11, wherein the component is selected from the group consisting of a health enhancing component and a comfort enhancing component.

19. An article to be worn by a user, the article comprising:

an article body that at least partially covers an appendage when worn;

at least one article fastener disposed on the article; and a plurality of layers including at least one longitudinally extending layer having at least one health enhancing component;

wherein the article fastener removably attaches the plurality of layers to the article; and wherein the component is removably attached to the longitudinally extending layer.

20. The article of claim 19, wherein said plurality of layers further includes a cushioning layer.

* * * * *